US009381053B2

(12) United States Patent
Parsons et al.

(10) Patent No.: US 9,381,053 B2
(45) Date of Patent: Jul. 5, 2016

(54) BONE PLATE WITH SUTURE HOLES FOR SOFT TISSUE REATTACHMENTS ON THE DIAPHYSEAL REGION OF THE PLATE

(71) Applicant: Arthrex, Inc., Naples, FL (US)

(72) Inventors: Bradford O. Parsons, Irvington, NY (US); Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 210 days.

(21) Appl. No.: 14/072,293

(22) Filed: Nov. 5, 2013

(65) Prior Publication Data

US 2014/0128921 A1    May 8, 2014

Related U.S. Application Data

(60) Provisional application No. 61/723,500, filed on Nov. 7, 2012.

(51) Int. Cl.
  *A61B 17/80*  (2006.01)
  *A61B 17/84*  (2006.01)
  *A61B 17/82*  (2006.01)

(52) U.S. Cl.
  CPC ............. *A61B 17/8061* (2013.01); *A61B 17/80* (2013.01); *A61B 17/82* (2013.01); *A61B 17/842* (2013.01)

(58) Field of Classification Search
  CPC ....................................................... A61B 17/82
  See application file for complete search history.

(56) References Cited

U.S. PATENT DOCUMENTS

| 6,716,234 | B2 | 4/2004 | Grafton et al. |
| 7,892,256 | B2 | 2/2011 | Grafton et al. |
| 8,298,284 | B2 | 10/2012 | Cassani |
| 8,439,976 | B2 | 5/2013 | Albertorio et al. |
| 8,460,379 | B2 | 6/2013 | Albertorio et al. |
| 2005/0182405 | A1* | 8/2005 | Orbay et al. ..................... 606/69 |
| 2006/0276896 | A1* | 12/2006 | Fallin et al. ................ 623/16.11 |
| 2007/0270853 | A1* | 11/2007 | Leung ................... A61B 17/80 606/280 |
| 2008/0140127 | A1 | 6/2008 | Vasta et al. |
| 2011/0144699 | A1 | 6/2011 | Fallin et al. |
| 2012/0095464 | A9 | 4/2012 | Zeiler et al. |

FOREIGN PATENT DOCUMENTS

EP    1 743 586 A1    1/2007
EP    1 764 053 A1    3/2007

* cited by examiner

*Primary Examiner* — Andrew Yang
(74) *Attorney, Agent, or Firm* — Blank Rome LLP

(57) ABSTRACT

A bone plate configured to accommodate flexible strands (flexible loops) attached to soft tissue to be attached to bone. The bone plate has a plurality of recessed eyelets on the distal edge of the plate, to allow the user (surgeon) to pass a flexible strand through the recessed eyelets and reattach the soft tissue to the plate at the anatomical location where the tissue was dissected. The recessed eyelets may have various shapes, forms and configurations and may be provided on or within a surface of the bone plate in any number, depending on the characteristics of the fractured bone or bone segments, or of the plate design. The eyelets preferably receive a flexible strand for fixation of soft tissue to the bone plate.

3 Claims, 5 Drawing Sheets

BONE PLATE WITH SUTURE HOLES FOR SOFT TISSUE REATTACHMENTS ON THE DIAPHYSEAL REGION OF THE PLATE

CROSS-REFERENCE TO RELATED APPLICATIONS

This application claims the benefit of U.S. Provisional Application No. 61/723,500, filed Nov. 7, 2012, the disclosure of which is incorporated by reference in its entirety herein.

FIELD OF THE INVENTION

The present invention relates to methods and apparatus for surgical procedures.

BACKGROUND OF THE INVENTION

Fractured bones are often treated using fixation devices that reinforce the fractured bone and keep the fractured segments aligned during healing. The fixation devices may take a variety of forms, including casts for external fixation and bone plates for internal fixation. Bone plates are typically formed as rigid metal plates that are mounted on a fractured bone or bone segments to span or bridge the fracture. Typically, the bone plates are held in place by screws or other fasteners attached to the bone on each side of the fracture through apertures in the bone plate.

Bone plates are considered the treatment of choice for many fractured bones, especially long bones, because they are compact, permitting an early return to motion. During the fracture repairs, surgeons often need to dissect the soft tissue from the bone to help seat the bone plate properly onto the bone.

There is a need for a bone plate provided with a new design that allows surgeons to reattach the soft tissue at the anatomic location where it was dissected. Also needed is a method of fracture repair that allows securing of dissected soft tissue to the anatomic position where it was dissected, during the fracture repair.

SUMMARY OF THE INVENTION

The present invention provides apparatus and methods for bone-tissue fixation using a bone plate having a plurality of recessed eyelets on the distal edge of the plate, to allow the user (surgeon) to pass a flexible strand through the recessed eyelets and reattach the soft tissue to the plate at the anatomical location where the tissue was dissected.

The bone plate of the present invention includes a body preferably formed of a metal and a plurality of eyelets (suture eyelets, apertures or holes) or other similar features which are incorporated into the shaft (diaphyseal region) of the plate, to allow soft tissue attachment in the shaft of the plate and reattachment of soft tissue that was dissected to fit the plate. The eyelets may have various shapes, forms and configurations and may be provided on or within a surface of the bone plate in any number, depending on the characteristics of the fractured bone or bone segments, or of the plate design. The eyelets preferably receive a flexible strand for fixation of soft tissue to the bone plate.

The present invention also provides a method for fixation of anatomical tissue during surgical applications by employing a bone plate having suture fasteners (eyelets) that allow reattachment of soft tissue to bone and to the plate. The method comprises the steps of: (i) providing a bone plate that includes a plurality of recessed eyelets on a diaphyseal region of a bone plate; (ii) assessing and reducing the bone fracture; (iii) placing the bone plate on the fractured bone and dissecting the adjacent soft tissue to allow the plate to fit; (iv) fixating the plate to bone; and (v) passing at least one flexible strand through the dissected soft tissue and through at least one of the recessed eyelets of the plate, and securing the dissected soft tissue to the anatomical position/location where it was dissected.

These and other features and advantages of the invention will be more apparent from the following detailed description that is provided in connection with the accompanying drawings and illustrated exemplary embodiments of the invention.

DETAILED DESCRIPTION OF THE INVENTION

Figure 1:
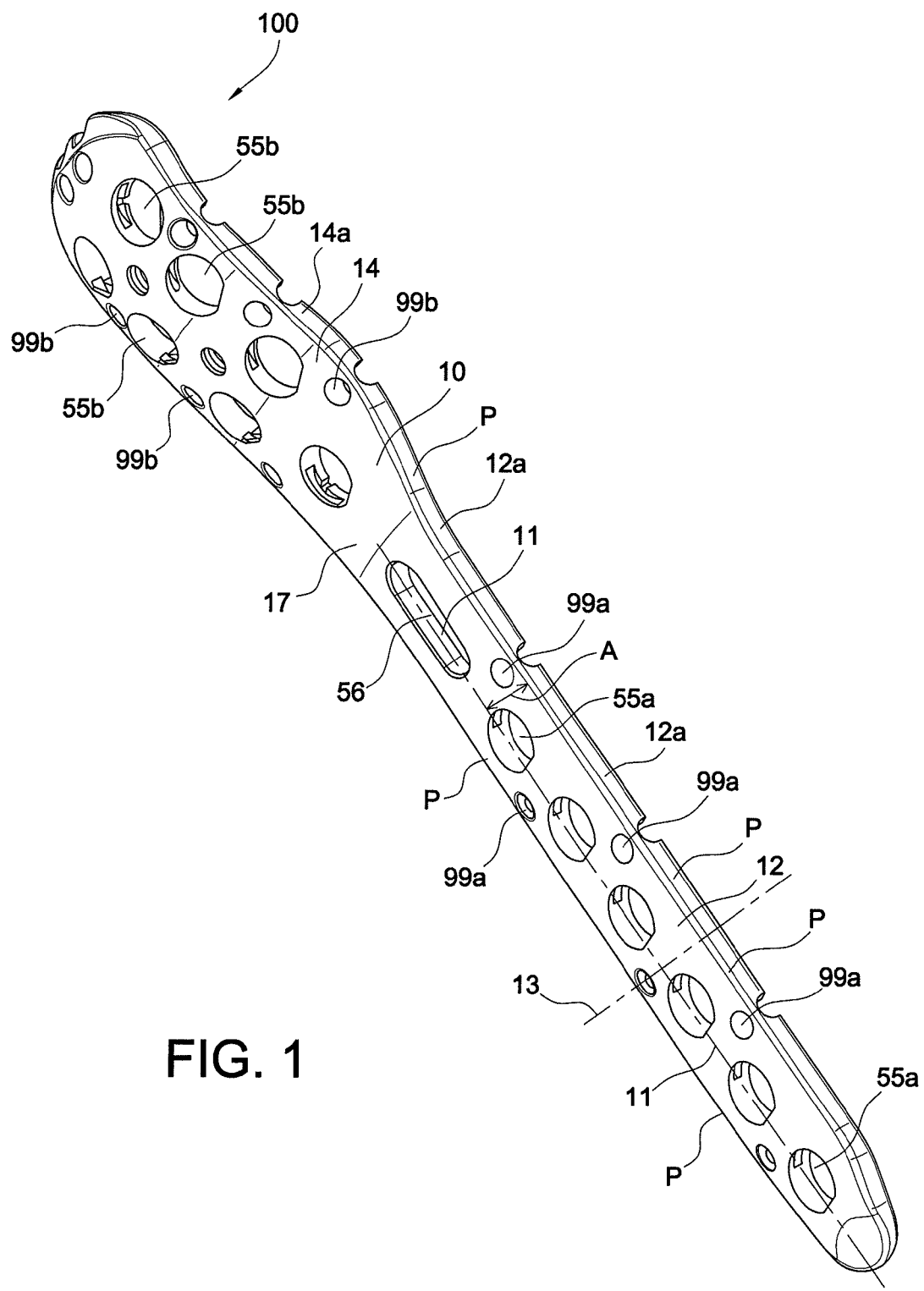
FIG. 1 illustrates a perspective view of an exemplary embodiment of a bone plate of the present invention.
Figure 2:
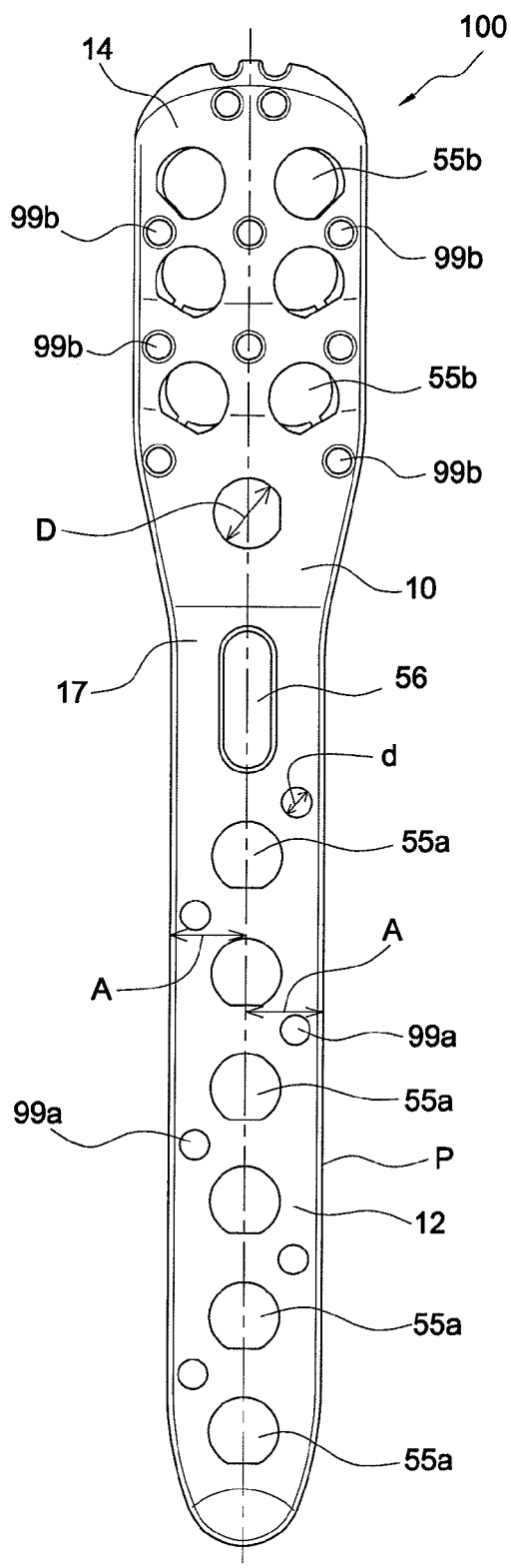
FIG. 2 illustrates a top view of the bone plate of FIG. 1.
Figure 3:
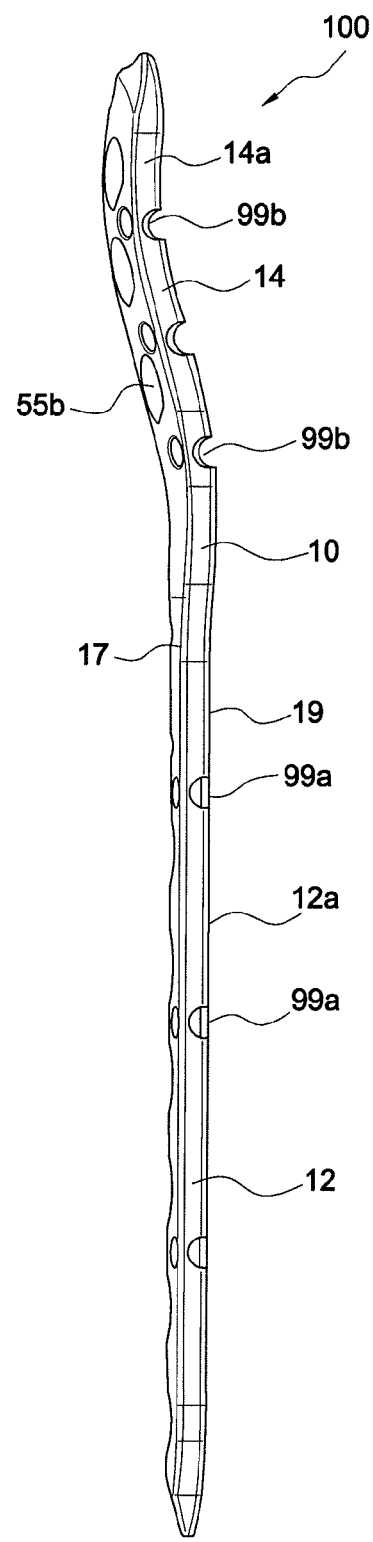
FIG. 3 illustrates a side view of the bone plate of FIG. 1.

The present invention provides a bone plate (suture plate) having a plurality of recessed suture eyelets on the plate, to allow the user (surgeon) to reattach the soft tissue to the plate and to the anatomical location where the tissue was dissected. The suture plate of the present invention is an improved fracture management system which is an anatomically designed, low profile, polyaxial locking plate/screw system that also provides and facilitates suturing of soft tissue to the plate after the plate has been positioned in place. Multiple chamfered suture eyelets provided along the margin of the plate allow the surgeon to pass flexible strands (for example, suture such as FiberWire® suture) after the plate is fixed to bone. The chamfered suture eyelets incorporate the flexible strands to the plate.

The bone plate of the present invention includes a body preferably formed of a metal and a plurality of suture eyelets (suture apertures/openings/holes) or other similar features which are incorporated into the shaft (diaphyseal region) of the plate, to allow soft tissue attachment in the shaft of the plate and reattachment of soft tissue that was dissected to fit the plate. The suture eyelets (holes) may have various shapes, forms and configurations and may be provided on or within a surface of the bone plate in any number, depending on the characteristics of the fractured bone or bone segments, or of the plate design. The suture eyelets preferably receive a flexible strand for fixation of soft tissue to the bone plate.

The present invention also provides a method of forming a bone plate having suture holes/apertures/openings for soft tissue attachment (or reattachment) for surgical application. A plurality of suture eyelets are formed along the periphery of a bone plate (distally) to enable a surgeon to easily place the muscles to be reattached (for example, the pectoralis or deltoid muscles) back to the bone (for example, humerus) during a fracture repair procedure.

The present invention also provides a method for fixation of anatomical tissue during surgical applications by employing a bone plate having suture fasteners (eyelets) that allow reattachment of soft tissue to bone and to the plate. The method comprises the steps of: (i) providing a bone plate that includes a plurality of recessed suture eyelets on a diaphyseal region of a bone plate; (ii) assessing and reducing the bone fracture; (iii) placing the bone plate on the fractured bone and dissecting the adjacent soft tissue to allow the plate to fit; (iv) fixating the plate to bone with fixation devices (for example, fasteners such as screws, anchors or washers); (v) passing at least one flexible strand (for example, suture) through the dissected soft tissue and through the recessed suture eyelets of the plate; and (vi) tying the at least one flexible strand (for example, suture) to secure the dissected soft tissue to the anatomical position/location where it was dissected.

Referring now to the drawings, where like elements are designated by like reference numerals, FIGS. 1-6 illustrate bone plate 100 of the present invention provided with a plurality of recessed eyelets 99a, 99b (recessed openings/apertures/holes 99a, 99b) incorporated into the plate to allow soft tissue attachment in the shaft of the plate.

For exemplary purposes only and for simplicity, the bone plate 100 is illustrated and described below as a bone plate for providing fixation of fractured humerus or of fractured humeral segments, and attachment of dissected pectoralis and/or deltoid muscles to the bone plate. However, the invention has applicability to the fixation of other bones or bone segments, including the fixation of associated soft tissue to bones or bone segments. Thus, the invention is not limited to this exemplary-only embodiment, and has applicability to any fracture repairs with the suture plate of the present invention.

As shown in FIGS. 1-4, the bone plate 100 (suture plate 100) includes a rigid body 10 with a longitudinal axis 11, a transversal axis 13, a first surface 17 and a second bone-contacting surface 19. Body 10 is preferably formed of a metal such as titanium, titanium alloy, stainless steel, or other materials that possess mechanical and physical properties suitable for coupling bones together. Body 10 is also defined by a distal region 12 (diaphyseal region 12 or shaft 12) surrounded by a distal edge 12a and a proximal region 14 surrounded by a proximal edge 14a. Proximal region 14 has a generally convex configuration.

The body 10 of the bone plate 100 is provided with a first plurality of through holes or openings 55a, 55b that receive corresponding fixation devices 60a, 60b (for example, screws, anchors and/or washers) to secure the bone plate to bone. The first plurality of openings 55a, 55b extend from the first surface 17 through the body 10 and to the bone-contacting surface 19, for accommodating at least one fixation device. Openings 55a, 55b may be provided in any number and may have similar or different perimeters. Openings 55a, 55b may be also optimally placed in the body 10 of the bone plate and at various angles with respect to transversal axis 13 of the bone plate 100.

The first plurality of openings 55a, 55b includes a first set of holes 55a (distal apertures 55a) located within the distal region 12 (diaphyseal region 12) and extending along the longitudinal axis 11 of the body 10, and a second set of holes 55b (proximal apertures 55b) located within the proximal region 14 and about parallel to each other and in symmetry relative to the longitudinal axis 11 of the body 10.

At least one of the openings 55a, 55b may include spherical bushings to allow variable angle-locking to be achieved by threading at least one tapered locking screw into the spherical bushings, as detailed below. The tapered head will expand the bushing, locking the screw to the plate. Non-locking screws may be also employed and can be placed in any opening 55a, 55b.

If polyaxial bushings is employed, the polyaxial bushings offer the surgeon the freedom to direct the fixation devices (for example, screws) within the anatomical template, based on the fracture pattern and bone quality for better fixation and to achieve a low profile polyaxial suture plate with any angulation, for example, a 60 degree angulation. The polyaxial bushings in each hole provide multi-directional locking or non-locking capability of the plate/screw construct to the bone. Drill guides can angulate the bushing to the desired screw trajectory.

As also shown in FIGS. 1-4, the bone plate 100 (suture plate 100) also includes a second plurality of apertures or recessed suture eyelets 99a which are disposed on the periphery of the shaft 12 (diaphyseal region 12 or distal region 12) of the bone plate 100, preferably on the distal edge 12a of the distal region 12 of the body 10. If desired, and as also shown in FIGS. 1-4, recessed suture eyelets 99b may be also provided around the proximal edge 14a of the proximal region 14 of the body 10.

Recessed suture eyelets 99a, 99b extend from the first surface 17 through the body 10 and to the bone-contacting surface 19, and around at least a margin (at least a length of a perimeter) of the rigid body 10, to accommodate at least one flexible strand attached to soft tissue to be attached to the rigid body and to the bone. Although reference to the eyelets 99a, 99b will be made below as to the suture eyelets 99a, 99b, the invention is not limited to this exemplary-only embodiment and contemplates eyelets for passing of any flexible strand, for example, suture, suture tape such as FiberTape®, suture chain such as FiberChain®, or a flexible material forming (or part of) a continuous loop/button construct provided with a button and a continuous loop attached to the button, among many others.

Figure 4:
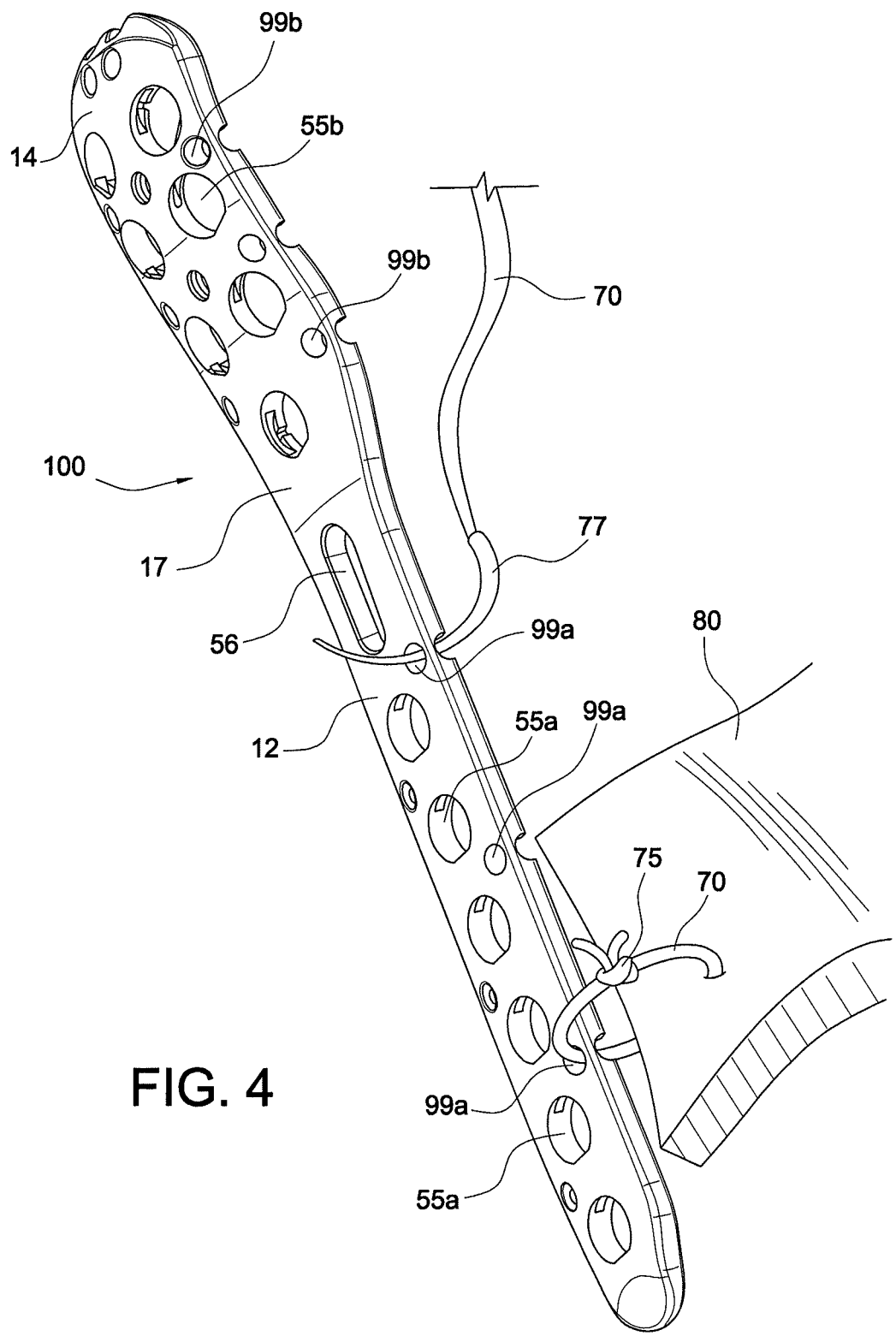
FIG. 4 illustrates the bone plate of FIG. 1 with exemplary tissue attached to the diaphyseal region of the plate.

Suture eyelets 99a, 99b are multiple chamfered suture eyelets provided along the margin (perimeter) of the plate 100 to allow the user (surgeon) to pass one or more flexible strands (for example, one or more suture strands such as FiberWire® suture) after the plate is fixed to bone. In this manner, suture eyelets 99a, 99b allow the user (surgeon) to reattach soft tissue 80 to the plate at the anatomical location where the tissue was dissected. The recessed suture eyelets 99a, 99b (holes/apertures/openings or chamfered suture eyelets 99a, 99b) may have various shapes, forms and configurations and may be provided on or within a surface of the bone plate 100 in any number, depending on the characteristics of the fractured bone or bone segments, or of the plate design. The suture eyelets 99a, 99b preferably receive at least one flexible strand 70 (FIG. 4) for fixation of soft tissue 80 to the bone plate 100. The flexible strand 70 may form one or more knots 75, as shown in FIG. 4. One or more flexible strands may be passed through a suture eyelet. One flexible strand may be passed through one or more suture eyelets.

In an exemplary embodiment, the second plurality of recessed suture eyelets 99a, 99b are provided along the margin/perimeter/periphery of the plate 100 in an area A (margin area A) lying beyond the strict limits of the lateral distal edge 12a of the plate 100, as shown in FIG. 1. The width of margin area A is about 1 to about 6 mm, preferably about 2 to about 4 mm to allow positioning of the recessed suture eyelets 99a, 99b within the area A and close to the lateral margin/edge 12a of the distal region or end 12 (diaphyseal region 12). In another embodiment, the recessed suture eyelets 99a, 99b are provided on the surface of the diaphyseal region 12 and just off the immediate perimeter P (FIG. 1) of the diaphyseal region 12. The recessed suture eyelets 99a, 99b may be provided on or within the surface of the diaphyseal region 12 of the bone plate 100.

In an exemplary embodiment, the first plurality of openings 55a, 55b have a first uniform diameter "D" (FIG. 2) and the second plurality of recessed suture eyelets 99a, 99b have a second uniform diameter "d" (FIG. 2) which is smaller than the first diameter "D." The first diameter "D" is preferably at least twice larger than the second diameter The present invention also provides a suture plate kit (assembly) with a bone plate 100 (suture plate 100) of the present invention and a suturing kit including at least one flexible strand attached to at least one needle. The at least one flexible strand may be FiberWire® suture containing color coded suture, for example, a #2 and/or #5 FiberWire® sutures, with needles on each end., to facilitate suturing the soft tissue to the bone plate after the plate is in place. The needles may be attached to the suture by any method known in the art, for example, by being swedged onto the suture, as shown in FIG. 4, for example. FIG. 4 illustrates exemplary bone plate 100 of the present invention with tissue 80 attached to its diaphyseal region 12 and illustrating exemplary curved needle 77 with attached suture 70 passed through one of the suture eyelets 99a for further attachment of soft tissue to plate 100.

The present invention also provides a method of forming a bone plate having suture holes for soft tissue attachment (or reattachment) for surgical application. A plurality of suture eyelets 99a, 99b (holes 99a, 99b) are formed along the periphery of a bone plate (distally) to enable a surgeon to easily place the soft tissue 80 to be reattached (for example, the pectoralis or deltoid muscles) back to the bone (for example, humerus) during a fracture repair procedure.

To secure longer bone plates to bone fractures, it is often necessary to partially or completely release the muscles adjacent the fractured bone, at the insertion of these muscles to the bone. For example, in the case of a humeral fracture, it is often necessary to partially or completely release (dissect) the deltoid and pectoralis muscles (soft tissue 80) attached to the humerus, to allow the plate to be appropriately placed. Bone plate 100 provided with suture eyelets 99a enables a surgeon to easily reattach these muscles back to the humerus and to repair the dissected muscles (the deltoid and pectoralis). The recessed suture eyelets 99a allow the surgeon to reattach the soft tissue 80 to the plate at the anatomical location where the soft tissue 80 was dissected. Preferably, the recessed suture eyelets 99a are placed more distal along the diaphyseal aspect of the plate 100, so as to be able to repair the pectoralis or deltoid muscles. Having suture holes 99a, 99b along the periphery of the plate distally confers the surgeon an easy place to reattach these muscles back to the humerus.

Figure 5:
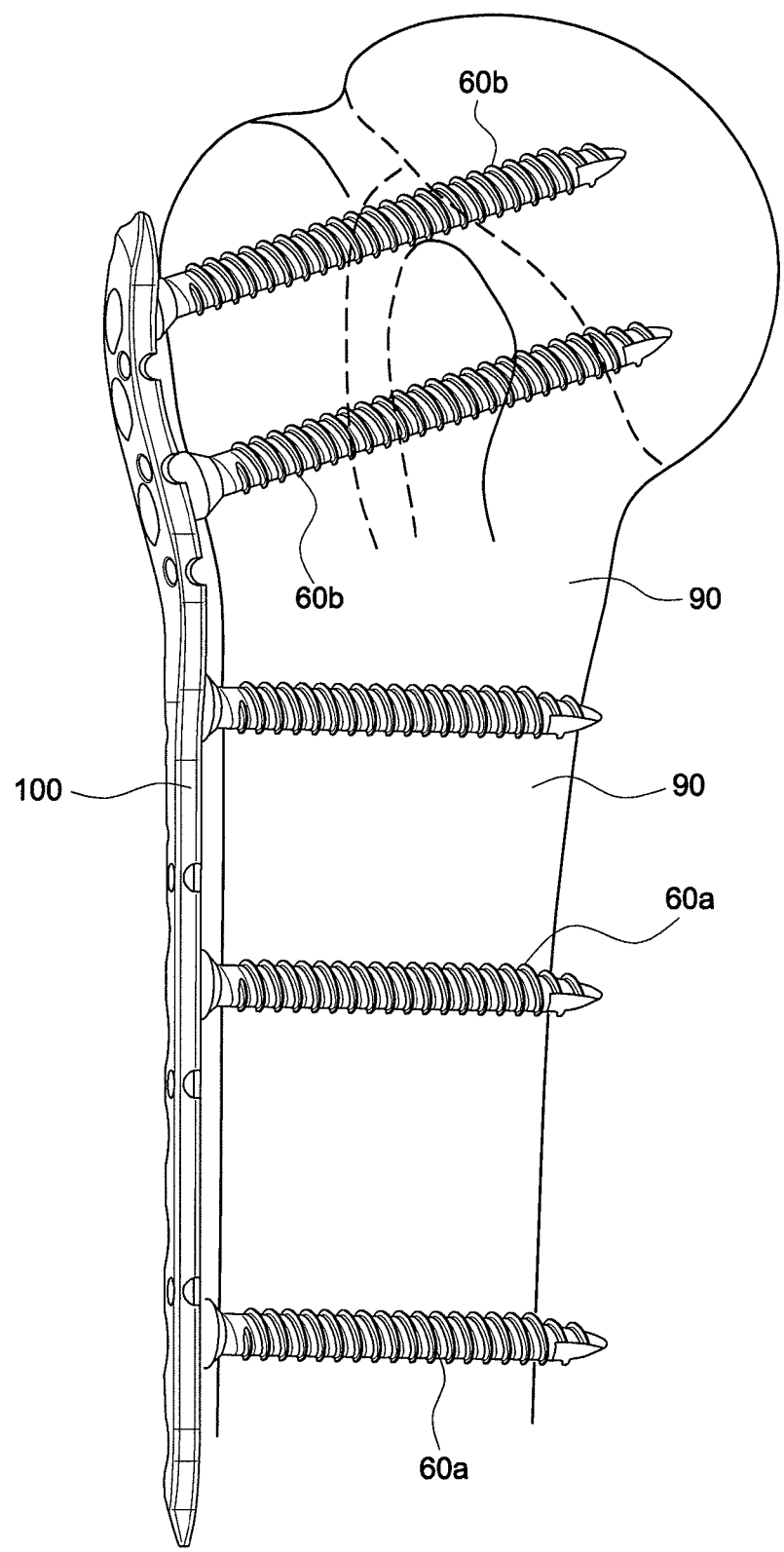
FIGS. 5 and 6 illustrate method steps of fracture repair and soft tissue reattachment (to the anatomical position where it was dissected) with an exemplary bone plate of the present invention.
Figure 6:
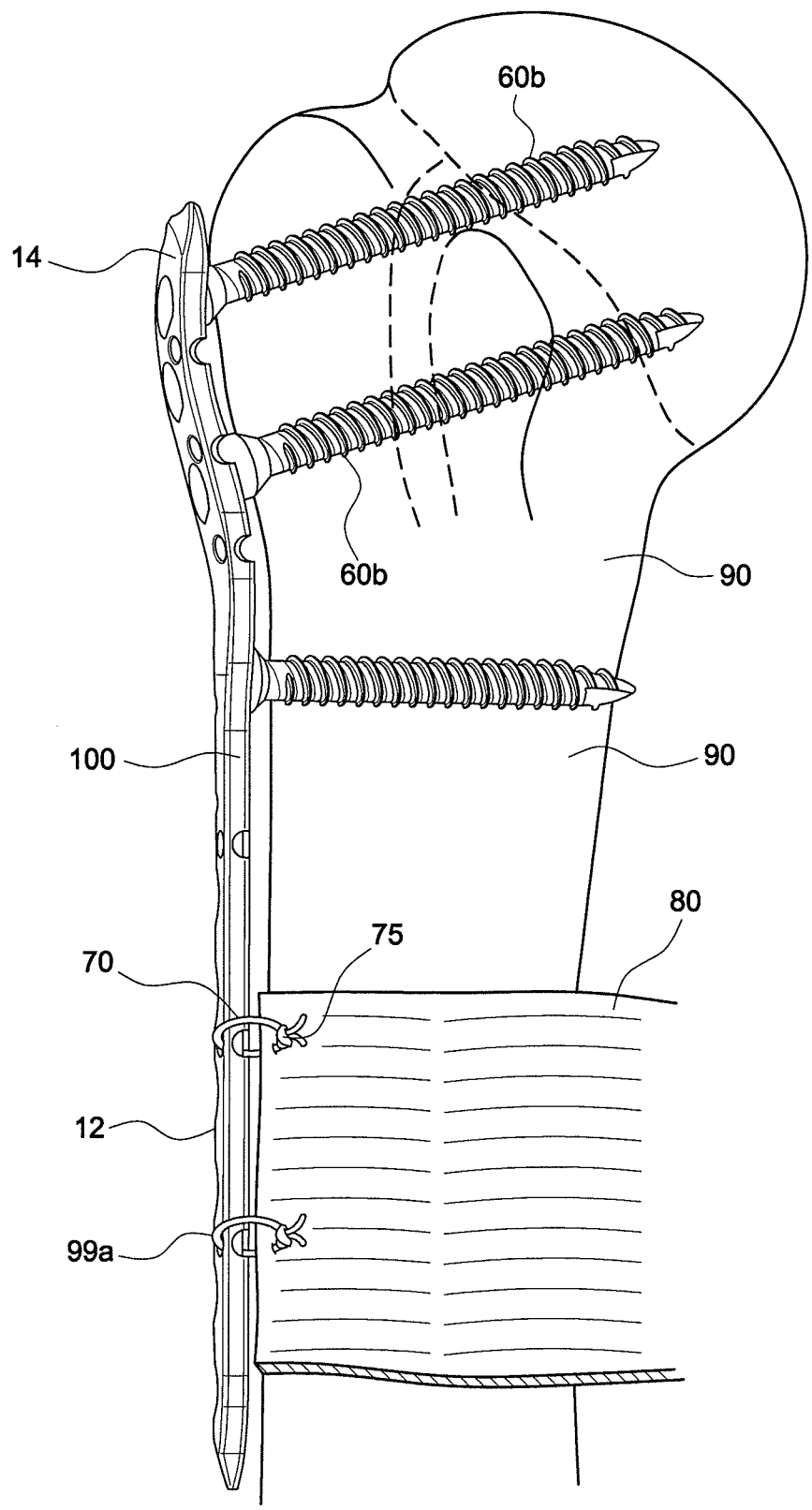

FIGS. 5 and 6 illustrate bone plate 100 (suture plate 100) of the present invention employed in an exemplary humeral fracture repair and soft tissue reattachment. Once distal and proximal screw fixation/placement have been conducted (FIG. 5), the repair is reinforced by attaching (suturing) the soft tissue 80 to the plate (FIG. 6). For humeral repair, soft tissue 80 to be attached to plate 100 is preferably the pectoralis (for example, pectoralis major) or deltoid muscle. The needles 77 are size-matched to the multiple chamfered holes 99a along the margin of the plate, allowing the sutures 70 to be passed after the plate 100 is securely fixed to the bone 90.

The bone plate of the present invention may optionally include spaced apart superior holes 99b that are used for supraspinatous repairs. The current existing superior holes are at the very top of the plate and they are a little close together, which makes using them suboptimal. Specifically, when the surgeon brings the sutures from the supra tendon to the plate, the narrow gap created between the two superior holes often causes the tendon to roll or bunch up, which leads to tendon injury in the postop period. Spacing the holes similarly to the other suture holes 99a, and/or chamfering the holes slightly to widen their position, eliminates the bunching effect.

For fractures of the greater tuberosity, suture 70 (for example, FiberWire® suture 70) may be also passed through one of the upper lateral suture holes and then through the supra and/or infraspinatus tendons adjacent to the bone/tendon junction. The FiberWire® is passed back through one of the suture holes on the plate and tied. For fractures of the lesser tuberosity, FiberWire® is passed through the subscapularis tendon at the tendon bone interface in a similar fashion. For fractures of the greater tuberosity, a #5 FiberWire® may be employed for use with the suture plate 100. It has a large cutting needle on one end for tissue passage and a smaller needle on the other end for passage through the plate.

An exemplary method for fixation of anatomical tissue during surgical applications employs bone plate 100 having suture fasteners 99a, 99b (eyelets 99a, 99b) that allow reattachment of soft tissue to bone and to the plate. The method comprises the steps of: (i) providing a bone plate 100 that includes a plurality of recessed suture eyelets 99a on a diaphyseal region 12 of bone plate 100; (ii) assessing and reducing the bone fracture; (iii) placing the bone plate 100 on fractured bone 90 and dissecting the adjacent soft tissue 80 to allow the plate 100 to fit; (iv) fixating the plate 100 to bone with fasteners 60a, 60b such as screws, anchors and/or washers; (v) passing a flexible strand 70 through the dissected soft tissue 80 and through the recessed suture eyelets 99a of the plate, by employing a passing instrument 77 (for example, a curved needle 77); and (vi) tying the flexible strand 70 to form at least one knot 75 to secure the dissected soft tissue 80 to the anatomical position/location where it was dissected.

An exemplary method for fixation of anatomical tissue during a humeral fracture repair comprises the steps of:
(i) providing a bone plate 100 that includes a plurality of recessed suture eyelets 99a on a diaphyseal region 12 of the bone plate 100;
(ii) assessing and reducing the bone fracture (the fracture fragments can be provisionally fixed and manipulated with K-wires);
(iii) placing the bone plate 100 on fractured bone 90 and dissecting the adjacent soft tissue 80 to allow the plate 100 to fit (plate is placed about 5-8 mm distal to the upper edge of greater tuberosity at the rotator cuff insertion; plate is centered against the lateral aspect of the greater tuberosity, lateral to the bicipital grove; the deltoid insertion may need to be elevated for optimal placement of a 5-hole or 6-hole plate; a temporary compression device may be used through oblong hole 56 to easily manipulate the position of the plate, while compressing the shaft 12 to the bone 90);
(iv) fixating the plate 100 to bone 90 with distal screw fixation (distal fasteners such as distal screws 60a); the distal aspect of the plate is fixed to the distal shaft fragment using the elongated slot 56 and a cortical screw (for example, a 3.5 mm cortical screw) to help control the height of the plate; for the distal screw holes 55a, the screws 60a may be installed with a driver and may be exemplary 3.5 mm cortical locking screws; the screws may preferably be inserted flush with the bushing;
(v) fixating the plate 100 to bone 90 with proximal polyaxial screw placement (proximal fixation devices 60b such as non-locking cortical screws or 4 mm cancellous locking screws); the polyaxial bushings in each hole provide multi-directional locking or non-locking capability of the plate/screw construct to the bone; drill guides can angulate the bushing to the desired screw trajectory; the proximal fixation devices (screws) create a scaffold within the humeral head alongside and around the subchondral bone;

(vi) passing a flexible strand 70 through the dissected soft tissue 80 and through the recessed suture eyelets 99a of the plate, by employing a passing instrument 77 (for example, a curved needle 77); and (vii) tying the flexible strand 70 to form at least one knot 75 to secure the dissected soft tissue 80 to the anatomical position/location where it was dissected.

The at least one flexible strand 70 may be suture or a high-strength suture, such as FiberWire® suture, which is disclosed and claimed in U.S. Pat. No. 6,716,234, the entire disclosure of which is incorporated by reference in its entirety herein. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The at least one flexible strand 70 may be also suture tape such as FiberTape®, suture chain such as FiberChain®, or a flexible material that is part of a continuous loop/button construct provided with a button and a continuous loop attached to the button.

In another exemplary embodiment, the flexible strand 70 may be a continuous loop formed of a plurality of suture strands configured to separate from a single strand to a plurality of strands in a continuous loop. In yet another embodiment, the flexible strand is an adjustable loop (forming a TightRope® ACL construct) which consists of two interconnected, adjustable flexible loops formed by splicing a suture strand in a manner disclosed in U.S. Pat. No. 8,460,379 issued on Jun. 11, 2013 and U.S. Pat. No. 8,439,976 issued on May 14, 2013, the disclosures of both of which are incorporated by reference herein in their entireties.

The flexible strand 70 may be also part of a suture loop/needle construct similar to the FiberLoop® construct detailed and disclosed in U.S. Pat. No. 8,298,284 issued on Oct. 30, 2012, the disclosure of which is incorporated by reference herein in its entirety. The flexible strand may be suture tape such as FiberTape® (as disclosed in U.S. Pat. No. 7,892,256) or collagen tape, or combinations thereof.

The fixation devices/implants 60a, 60b may have various sizes (various diameters and/or lengths) and may be formed of biocompatible materials such as PEEK, biocomposite materials, metals and/or metal alloys, or combination of such materials, among others. The fixation devices/implants 60a, 60b may be also formed of any rigid medically approved materials, for example, plastic or carbon fiber, or combination of different materials.

The systems and methods of the present invention have applicability to any tissue repair and attachment of soft tissue to bone as part of fracture management repair, for example, knotted or knotless tissue repairs such as attachment of soft tissue to bone, with particular applications to the tissue being soft tissue or capsular tissue.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method of bone-tissue fixation, comprising the steps of:
   releasing or partially releasing soft tissue attached to a fractured bone;
   subsequently, placing a suture plate on the fractured bone and attaching the suture plate to the fractured bone; and
   attaching the released or partially released soft tissue to the suture plate by passing at least one flexible strand through the released or partially released soft tissue and through at least one chamfered suture eyelet located on the periphery of a diaphyseal region of the suture plate, wherein the bone is humerus and the soft tissue is deltoid or pectoralis muscle.

2. The method of claim 1, wherein the at least one flexible strand is a suture, suture tape, suture chain, or combinations thereof.

3. The method of claim 1, wherein the at least one flexible strand is part of a suture loop/button construct comprising a button and a continuous suture loop attached to the button, the continuous suture loop having an adjustable perimeter.

\* \* \* \* \*